United States Patent
Do et al.

(10) Patent No.: US 11,304,595 B2
(45) Date of Patent: Apr. 19, 2022

(54) WORKING CHANNEL ELEMENT, ENDOSCOPE WITH A WORKING CHANNEL ELEMENT, AND METHOD FOR USING A WORKING CHANNEL IN AN ENDOSCOPE

(71) Applicant: DIGITAL ENDOSCOPY GMBH, Friedberg (DE)

(72) Inventors: Anh Minh Do, Friedberg (DE); Tilman Schroeter, Friedberg (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 342 days.

(21) Appl. No.: 16/340,517

(22) PCT Filed: Oct. 27, 2017

(86) PCT No.: PCT/EP2017/077588
§ 371 (c)(1),
(2) Date: Apr. 9, 2019

(87) PCT Pub. No.: WO2018/083024
PCT Pub. Date: May 11, 2018

(65) Prior Publication Data
US 2019/0239728 A1    Aug. 8, 2019

(30) Foreign Application Priority Data

Nov. 4, 2016  (DE) .......................... 102016121056.0

(51) Int. Cl.
*A61B 1/00*   (2006.01)
*A61B 1/018*  (2006.01)
(Continued)

(52) U.S. Cl.
CPC ............ *A61B 1/018* (2013.01); *A61B 1/0014* (2013.01); *A61B 1/0051* (2013.01);
(Continued)

(58) Field of Classification Search
None
See application file for complete search history.

(56) References Cited

U.S. PATENT DOCUMENTS 6,059,719 A * 5/2000 Yamamoto ......... A61B 1/00059
600/104
6,099,464 A * 8/2000 Shimizu ............. A61B 1/00075
600/104

(Continued)

FOREIGN PATENT DOCUMENTS

JP  3595409 B2  12/2004
JP  6017741 B1  11/2016

OTHER PUBLICATIONS

U.S. Appl. No. 16/349,388 to Stefan Kolberg, which was filed on May 13, 2019.
(Continued)

*Primary Examiner* — Timothy J Neal
(74) *Attorney, Agent, or Firm* — Greenblum & Bernstein, P.L.C.

(57) ABSTRACT

The invention relates to a working channel element for an endoscope. The working channel element has a tubular shape, which has an inner circumference and an outer circumference and through which an instrument can be pushed. The working channel element is adapted to be temporarily inserted into a working channel of an endoscope with its distal side ahead.

10 Claims, 10 Drawing Sheets

(51) Int. Cl.
*A61B 1/005* (2006.01)
*A61B 17/00* (2006.01)

(52) U.S. Cl.
CPC ...... *A61B 1/00098* (2013.01); *A61B 1/00103* (2013.01); *A61B 1/00133* (2013.01); *A61B 1/00142* (2013.01); *A61B 2017/0034* (2013.01)

(56) References Cited

U.S. PATENT DOCUMENTS

| | | | | |
|---|---|---|---|---|
| 2005/0272975 | A1* | 12/2005 | McWeeney | A61B 6/06 600/172 |
| 2006/0149129 | A1* | 7/2006 | Watts | A61B 1/0676 600/113 |
| 2007/0255104 | A1* | 11/2007 | Maruyama | A61B 1/0052 600/148 |
| 2011/0099773 | A1* | 5/2011 | Golden | F16B 2/12 24/457 |
| 2012/0265132 | A1* | 10/2012 | Nomura | A61B 1/00098 604/95.04 |
| 2013/0012781 | A1* | 1/2013 | Kaneko | A61B 1/0057 600/148 |
| 2015/0057537 | A1* | 2/2015 | Dillon | A61B 1/0125 600/431 |
| 2016/0227988 | A1 | 8/2016 | Jiang et al. | |
| 2017/0095139 | A1 | 4/2017 | Yanagihara et al. | |
| 2019/0110661 | A1 | 4/2019 | Do et al. | |

OTHER PUBLICATIONS

U.S. Appl. No. 16/087,903 to Stefan Kolberg, which was filed on Sep. 24, 2018.
Search Report issued in International Bureau of WIPO Patent Application No. PCT/EP2017/077588, dated Jan. 8, 2018.

\* cited by examiner

WORKING CHANNEL ELEMENT, ENDOSCOPE WITH A WORKING CHANNEL ELEMENT, AND METHOD FOR USING A WORKING CHANNEL IN AN ENDOSCOPE

The present invention relates to a working channel element for an endoscope, and an endoscope having said working channel element. The present invention further relates to a method for using a working channel in an endoscope.

Such an endoscope may be, for example, a duodenoscope, that is an endoscope for examining, e.g., the esophagus or also the duodenum, the bile duct, the gall bladder, the pancreatic duct, the pancreas, etc. With the assistance of the duodenoscope, it is possible to reach the duodenum through the esophagus, the stomach, and the pyloric orifice.

The duodenoscope comprises (lateral) optical means (illumination means and a camera) directed to the side. This can make it difficult to introduce into the esophagus and advance it therein, since forward viewing is not easily possible. Merely the stomach or the duodenum offers sufficient room to bend the distal end of the duodenoscope by about 90°, thus allowing a forward view.

Further, at the exit of the working channel, the duodenoscope comprises an Albarran lever which, by pivoting, allows the tools that are being advanced through the working channel to be selectively redirected. Such an Albarran lever normally has a complex shape, which is difficult to clean.

With some duodenoscopes, the Albarran lever may be designed as a disposable element to better prevent the possibility of the adherence of microbes as occurs with a reusable endoscope.

However, even with these duodenoscopes, microbes can still be caught in the working channel.

After the duodenoscope has been used, it is subjected to reprocessing. Such reprocessing has to reliably exclude the transmission of all microorganisms, such as bacteria, viruses, fungi, worms, and even spores. During reprocessing, the duodenoscope, including the working channel, first undergoes manual cleaning so that organic material or chemical residues are completely removed. After cleaning, the duodenoscope is subjected to mechanical disinfection or sterilization.

It is the object of the present invention to provide an improved working channel and an improved endoscope in which the transfer of microbes is even more effectively prevented.

This object is achieved by a working channel element comprising the features of claim 1. An endoscope with the working channel element is indicated in claim 10. A method for using a working channel in an endoscope is indicated in claim 11.

Advantageous further developments are the subject matter of the dependent claims.

A working channel element according to the invention has a tubular shape, which has an inner circumference and an outer circumference, wherein an instrument can be pushed through the tubular shape. The working channel element is adapted to be temporarily inserted into a working channel of an endoscope with its distal side ahead.

The working channel element has an external dimension which enables insertion into a working channel of an endoscope. The working channel element is adapted to the shape of the working channel of the endoscope. The working channel element preferably has a round shape. The external dimension (e.g. the outer diameter) of the working channel element is thus slightly smaller than the internal dimension (e.g. inner diameter) of the working channel of the endoscope.

Thus, the invention may comprise an endoscope with a removable working channel which is not permanently attached.

This results in facilitated cleaning of the endoscope, because each patient can have their own working channel, which can be disposed of. Only the endoscope into the working channel of which the working channel element according to the invention has been introduced needs to be cleaned.

The working channel element may have a bending portion on the distal side. Thus, the working channel element itself can take on the task of bending of an inserted instrument, which previously had, e.g., an Albarran lever internally. The previous complex geometry of an Albarran lever can be dispensed with on the distal end of the endoscope in this case. Thus, the endoscope itself is also easier and more efficient to clean. Cross-contamination from patient to patient can be prevented even better.

The working channel element may have, on the proximal side, a control unit for controlling the bending of the bending portion. The control unit may be configured such that it tensions control wires guided in the working channel element between the inner circumference and the outer circumference and anchored at the bending portion, so as to control the bending of the bending portion. The bending of an inserted instrument can thereby be enabled advantageously and simply.

The control unit may be configured, e.g., as a slider in which the proximal end of the control wires is anchored.

The control unit may comprise a plurality of separate control elements, wherein at least one of the control wires is assigned to each separate control element.

The working channel element may comprise, on the proximal side, a locking means for fixing a bent position of the distal bending portion. By means of the locking means (e.g. a braking mechanism), physicians can then fix the position ideally bent for them and bring therapeutic instruments through the working channel to the desired position in the tissue.

The working channel element may comprise, on the proximal side, a mounting means by means of which the working channel element can be mounted to an endoscope. The working channel element according to the invention can thereby be quickly and stably mounted on the endoscope in a manner that the operator (physician) is familiar with. The mounting means of the working channel element according to the invention is preferably provided distally of a control unit of the working channel element.

An endoscope may be equipped with such a working channel element. The control unit for controlling the bending of the bending portion may be arranged close to a gripping portion of the endoscope such that the operator can comfortably reach and operate both the control portion of the endoscope as well as the control unit for controlling the bending of the bending portion (ideally with one hand). The endoscope may be any endoscope having its own working channel.

In a method according to the invention for using a working channel in an endoscope, a separate working channel element is temporarily inserted into a working channel of an endoscope with its distal side ahead.

The method may further comprise the following steps: Introducing the working channel element into the endoscope, and bending of a distal end of the working channel element into the desired position.

After the working channel element has been used once, the working channel element can be pulled out of the endoscope and disposed of.

After the working channel element has been used once, the working channel element can be pulled out of the endoscope on the distal side of the endoscope and disposed of. The used working channel element exits the endoscope on the distal side of the endoscope. Thus, microbes are not introduced in the endoscope in the proximal direction. Even better protection from contamination can thereby be obtained.

The previously explained aspects of the present invention may be suitably combined.

The present invention is described in more detail in the following by means of exemplary embodiments with reference to the drawings.

Exemplary Embodiment 1

Initially, a first exemplary embodiment of the present invention is described with reference to FIGS. 1 to 7.

Figure 1:
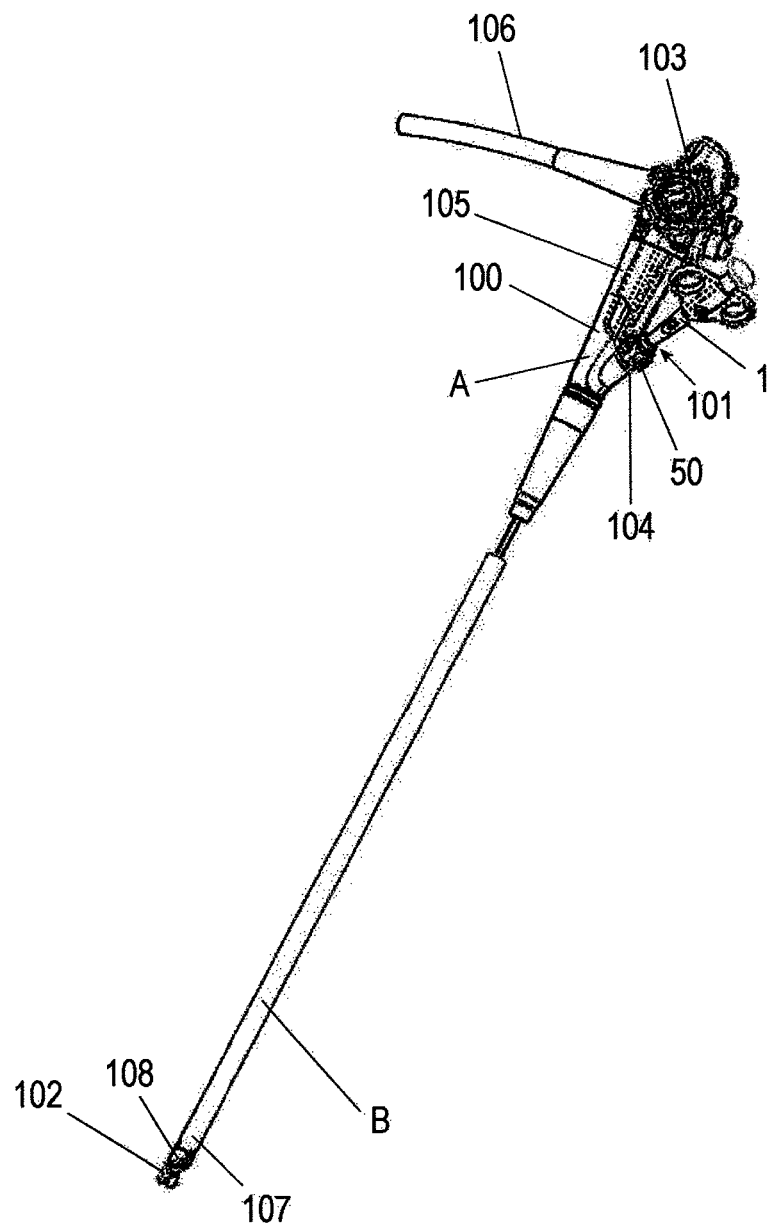
FIG. 1 shows a perspective view of a working channel element according to the invention of a first exemplary embodiment in a state in which it is installed in the endoscope.
Figure 2:
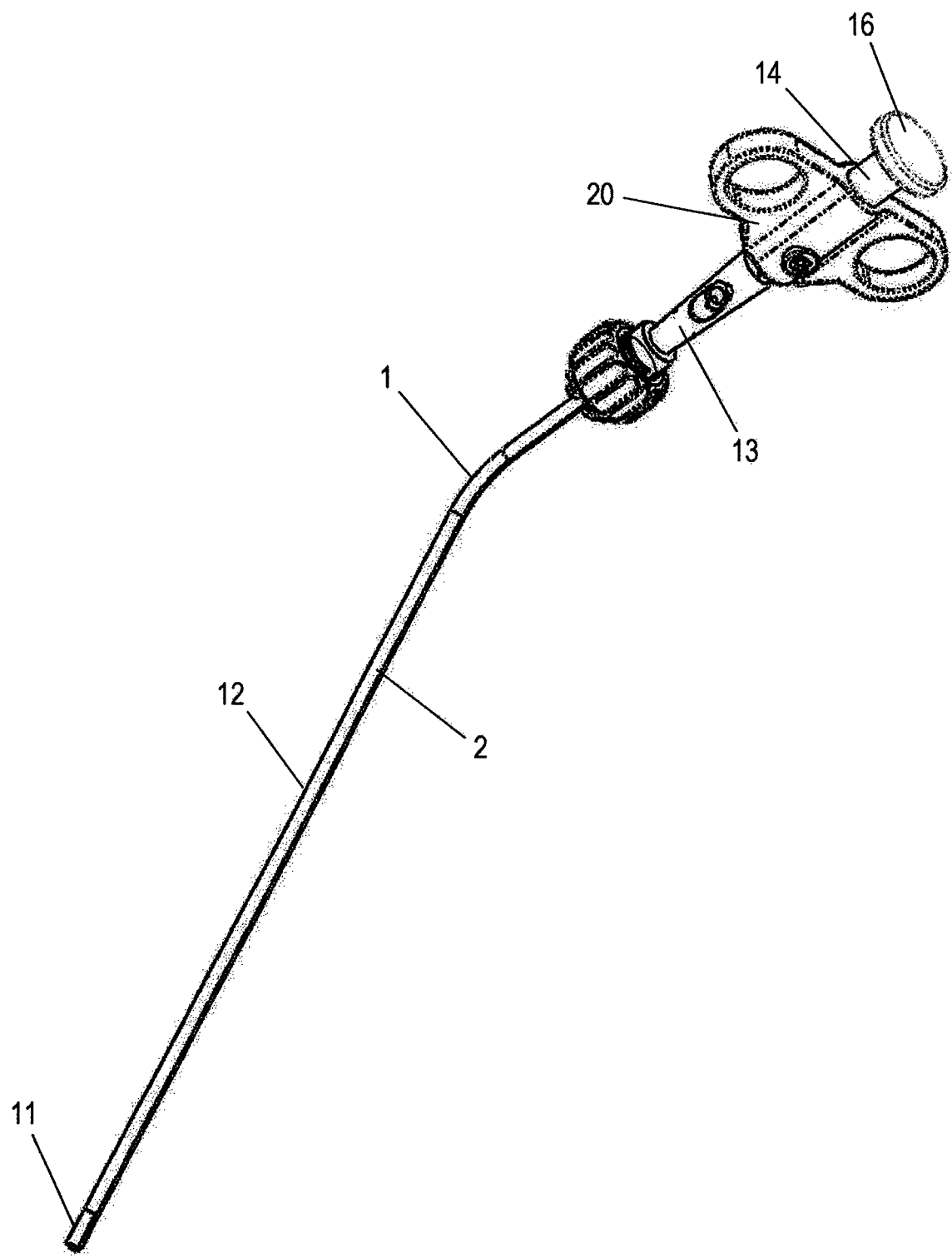
FIG. 2 shows a perspective view of the working channel element according to the invention of the first exemplary embodiment, separately from the endoscope, wherein the position of an ultrasound sensor is indicated.

FIGS. 1 and 2 each show a perspective view of a first exemplary embodiment of a working channel element 1 according to the invention. Specifically, FIG. 1 shows a state in which the working channel element 1 according to the invention is mounted on an endoscope, and FIG. 2 shows the working channel element 1 separately from the endoscope.

Firstly, an endoscope 100 is briefly described with reference to FIG. 1, in which the working channel element 1 according to the invention can be used. The endoscope 100 has a longitudinal endoscope body.

Said endoscope 100 is formed, e.g., as a flexible endoscope for the gastrointestinal tract. The endoscope has a control part A and an insertion portion B. The control part A is located on the proximal side and the insertion portion B is located on the distal side of the endoscope 100. The control part A has a working channel inlet 101 and an adjusting knob 103 for bending an endoscope bending portion on the distal end of the insertion portion B of the endoscope. The working channel inlet 101 is equipped with a connecting element 104, which may be in the form of a customary Luer-Lock connection. Furthermore, the control part A is equipped with a gripping portion 105, on which the operator holds the endoscope 100.

The control part A is connected to a video processor, a light source device, and a display unit, and the like via cable 106.

The insertion portion B is a long, tubular element. The proximal end of the insertion portion is connected to the control part A. The insertion portion B has a flexible portion and the endoscope bending portion 107, in the sequence as viewed from the control part A. The flexible portion is elastic. The endoscope bending portion 107 is bent in response to actuation of the adjusting knob 103. A rigid end piece portion is formed on the distal end of the endoscope bending portion 107. The rigid end piece portion forms the so-called endoscope head 108. An ultrasound sensor 102 is arranged on the distal end of the endoscope head 108.

The control part A has a angled access on the distal side of the gripping portion 105.

A working channel is provided in the endoscope 1. The working channel starts at the working channel inlet 101, which is formed on the proximal side of the angled access, continues through the angled access, opens into the control part A, and extends through the control part A in the distal direction, continues through the insertion portion B, and opens at the endoscope head 108 such that it is aligned (oriented) in the distal direction.

The working channel element 1 according to the invention and described as follows can be inserted into said working channel of the endoscope 1.

The working channel element 1 is shown separately from the endoscope in FIG. 2.

The working channel element 1 has a flexible tubular element 2. The flexible tubular element 2 is produced from an elastic material and preferably consists of plastic or rubber. The flexible tubular element 2 is formed as a cylinder-like tube with an inner circumference and an outer circumference. The outer circumference of the flexible tubular element 2 is smaller than the previously described working channel of the endoscope 1. The inner circumference of the flexible tubular element 2 has a size such that micro-tools for examining, e.g., the esophagus or also the duodenum, the bile duct, the gallbladder, the pancreatic duct, the pancreas etc. can be inserted and advanced.

Figure 12:
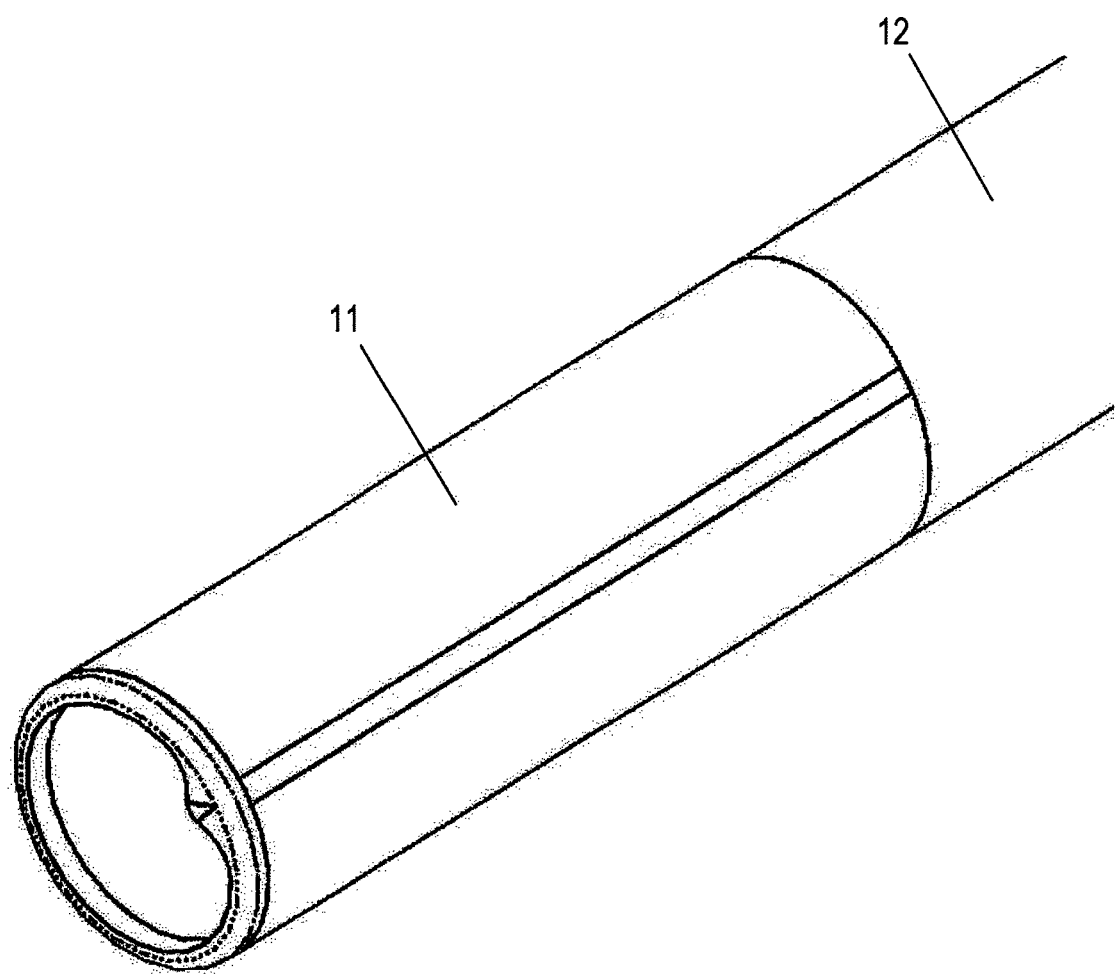
FIG. 12 shows a perspective view of the distal end portion of the working channel element according to the invention of the first exemplary embodiment.

The flexible tubular element 2 is formed on the proximal side as a main tube 12. On the distal side of the tubular element 2, the working channel element 1 has a bending portion 11, which connects distally to the main tube 12; also refer to FIG. 12.

The bending portion 11 is a bendable portion of the tubular element 2. On its proximal end, the bending portion 11 has a proximal annular element, to which the distal end of the main tube 12 is connected. On the distal end, the bending portion 11 has a distal annular element. The bending portion 11 can be bent (is bendable) between the proximal annular element and the distal annular element via tension wires (control wires) as described in the following.

Tension wires (control wires), not shown in the drawings, are arranged, extending in the longitudinal direction, between the inner circumference and the outer circumference of the tubular element 2 in the working channel element 1. At least one tension wire is used in the exemplary embodiment. In order to ensure the function of the bending portion 11, one tension wire is sufficient. In order to achieve finer (more precise) control of the bending of the bending portion 11, multiple tension wires can be used.

The tension wires of the working channel element 1 extend into tension wire channels or tension wire areas between the inner circumference and the outer circumference of the tubular element 2. Said tension wire channels or tension wire areas are sealed off to the environment, at least on the distal side of the working channel element 1.

In the present exemplary embodiment, one tension wire is provided in the working channel element 1 according to the invention. On the distal side of the tubular element 2, that is in the bending portion 11, the tension wire is guided to the distal annular element through the proximal annular element and the tubular piece of the bending portion 11 and anchored on the distal annular element. In other words, the distal annular element forms the distal anchoring point of the tension wire. The tension wire is thus arranged along the axial direction of the working channel element 1 and anchored on the distal side of the bending portion 11 and can be actuated by a control unit on the proximal side of the working channel element 1. This means that when the tension wire is pulled, the anchoring point on the distal side of the bending portion 11 of the working channel element 1 is pulled in the proximal direction, whereby the bending portion 11 is bent.

Thus, by pulling the tension wire, the lateral orientation of the bending portion 11 can be modified in a known manner. In other words, when the working channel element 1 of the bending portion 11 is inserted in the endoscope 100, the orientation angle of the micro-tools that are pushed through the inner channel 13 of the tubular element 2 is modified. The orientation of the micro-tools can thus be modified to the desired lateral direction by changing the angle of the bending portion 11 relative to the endoscope head 108. The micro-tools then protrude laterally from the endoscope head 108 in the selected angular position in order to be pushed into, e.g., a bile duct.

In the first exemplary embodiment, the distal end of the working channel element 1 is located proximally from the ultrasound sensor 102, when the working channel element 1 is inserted in the endoscope 100.

The configuration of the bending portion 11 so as to be bent and thus controlled is explained in the following with reference to FIGS. 3 to 6.

Figure 3:
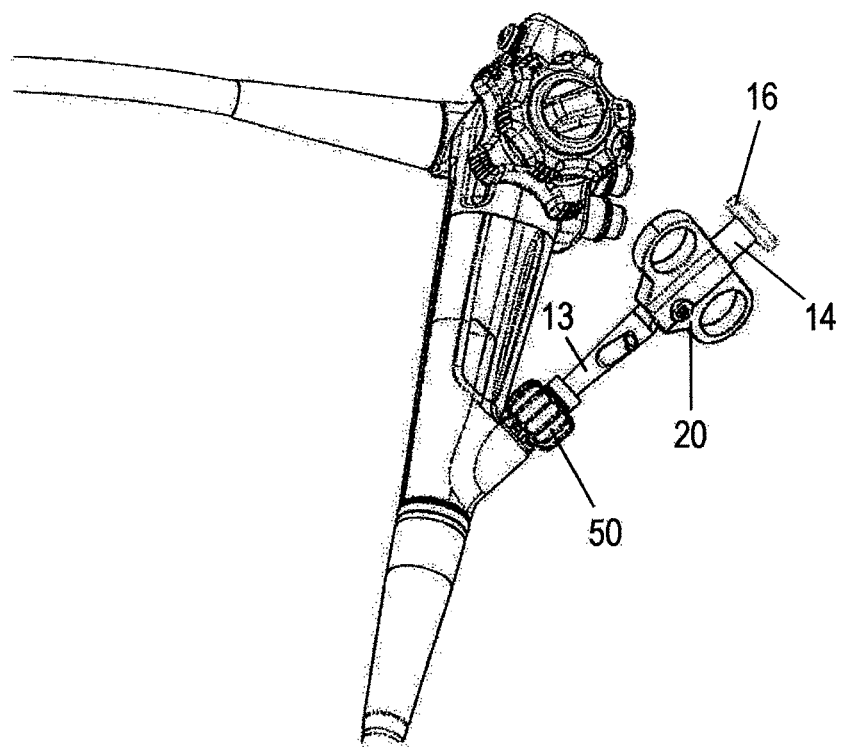
FIG. 3 shows a perspective view of a control unit of a working channel element according to the invention of the first exemplary embodiment.

The proximal side of the working channel element 1 is shown in FIG. 3.

The working channel element 1 has a transition element 13 on the proximal side of the tubular element 2. The transition element 13 is formed as a hollow element with a diameter that enlarges in the proximal direction.

Figure 4:
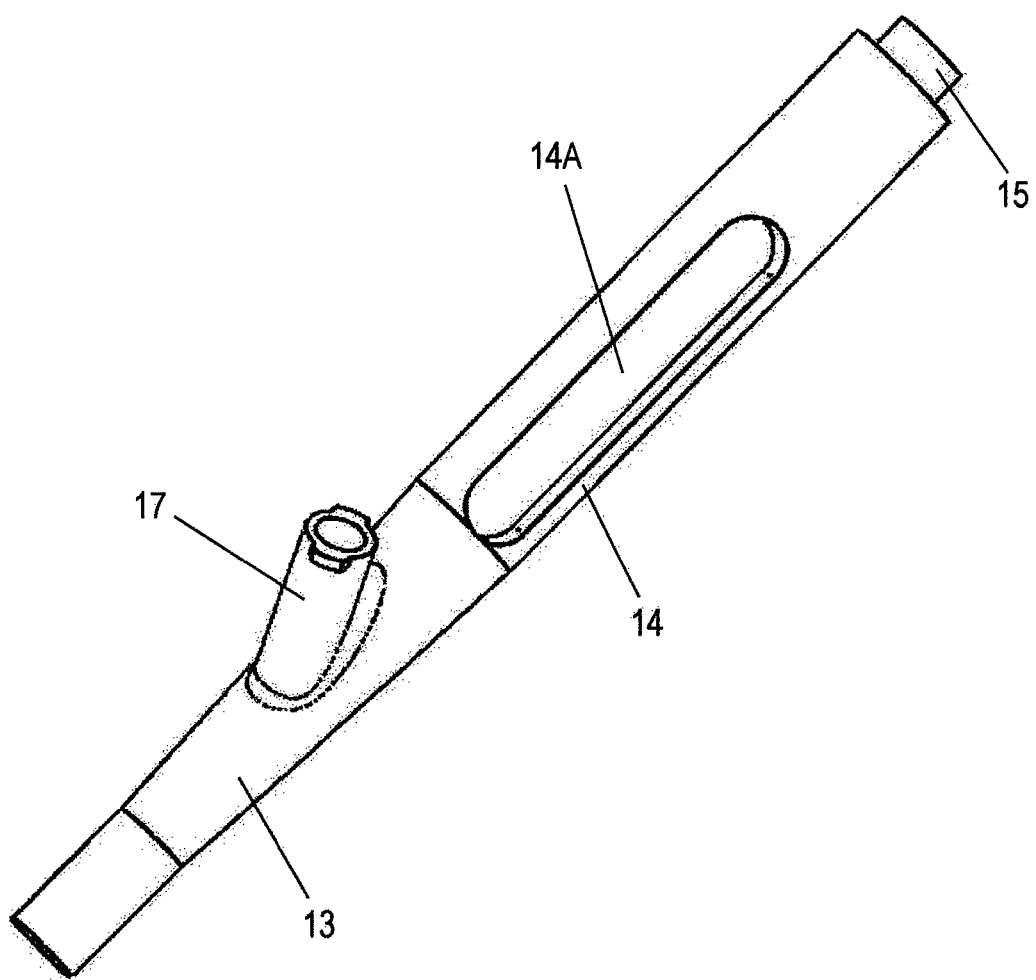
FIG. 4 shows a perspective view of a proximal end portion of the working channel element according to the invention of the first exemplary embodiment.
Figure 5:
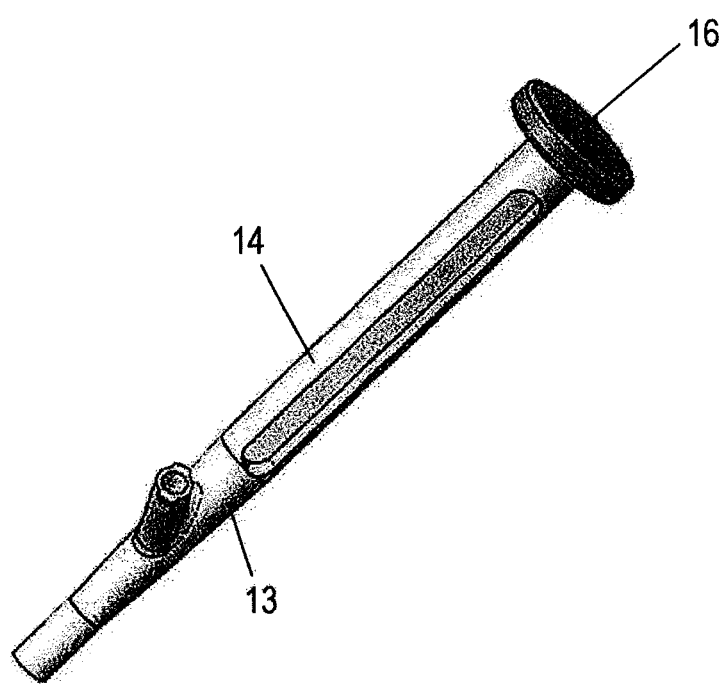
FIG. 5 shows a further perspective view of the proximal end portion of the working channel element according to the invention of the first exemplary embodiment.

A rod element 14 is provided proximally from the transition element 13. The rod element 14 is a hollow cylinder, which has a continuous lateral slit 14A extending in the longitudinal direction of the rod element 14, equipped with a base, as is shown in FIG. 4. The base of the rod element 14 points in the proximal direction. The rod element 14 opening opposite the base is connected to the transition element 13.

The proximal end of the tubular element 2, the transition element 13, and the rod element 14 are arranged on the same axis.

A nose 15, which points in the proximal direction, is arranged on the base of the rod element 14. A plate element 16, the proximal surface of which serves as a thumb-actuation surface, is placed on the nose 15; see FIG. 5.

The respective connection between the tubular element 2 and the transition element 13, between the transition element 13 and the rod element 14, and between the plate element 16 and the nose 15 can be created through gluing, laser treatment, soldering, or another suitable method. The plate element 16 can be attached or pressed onto the nose 15.

On the outer wall of the transition element 13, a tubular instrument access 17, which penetrates through the outer wall of the transition element 13, and through which the instruments, micro-tools etc. can be pushed into the inner channel of the tubular element 2, i.e. of the working channel element 1, in the distal direction, extends laterally from the transition element 13. The instrument access 17 can be attached to the transition element 13 by means of laser treatment, soldering, or a another suitable method.

The tension wire (or tension wires) penetrates the inner circumference of the working channel element 1 in the proximal end area of the tubular element 2 or in the area of the transition element 13 and extends to the control unit 20 as is described in the following. In order to prevent impacting instruments to be inserted, the location at which the tension wire penetrates the inner circumference of the working channel element 1 may be proximal from the instrument access 17.

A slider 20 is arranged, so as to slide, on the rod element 14 as a control unit in the longitudinal direction of the rod element 14. The slider 20 is explained in greater detail in the following by means of FIG. 6.

The slider 20 has a tubular portion 20A with an inner diameter that is slightly greater than the outer diameter of the rod element 14. The slider 20 can thereby be pushed on the rod element 14.

The slider 20 has a hole 20B, in the area of the tubular portion 20A, which extends perpendicular to the longitudinal axis of the tubular portion 20A and points in the radial, i.e. lateral, direction.

Figure 6:
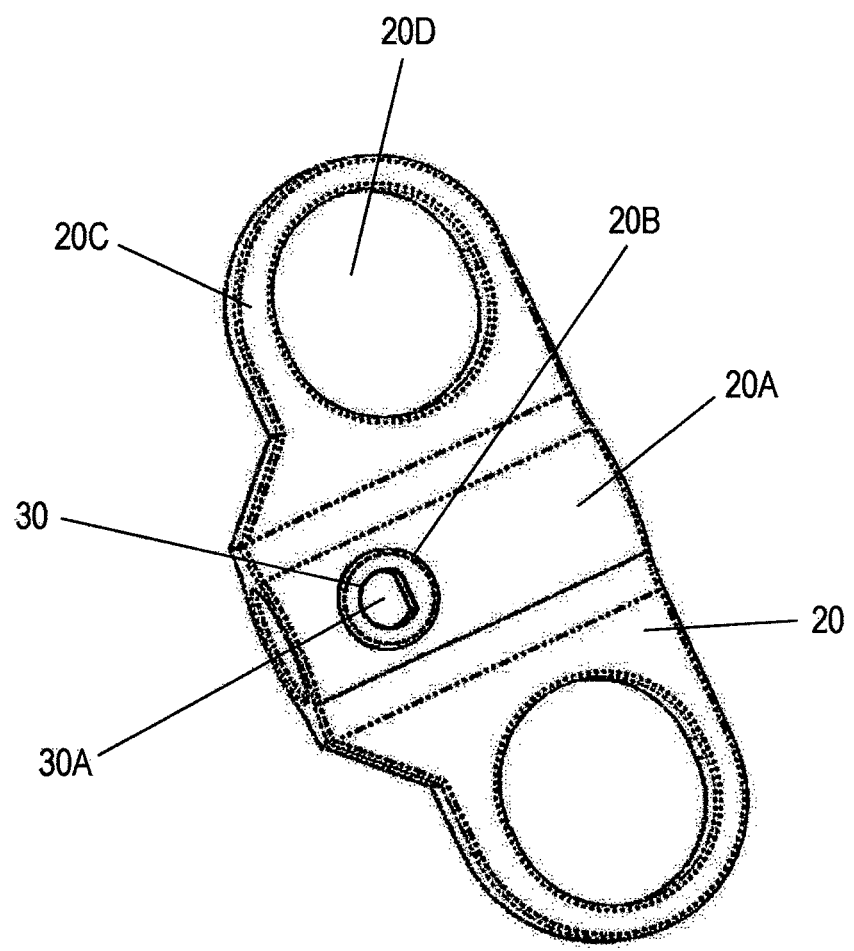
FIG. 6 shows a perspective view of a control element of the control unit of the working channel element according to the invention of the first exemplary embodiment.

Furthermore, two side wings 20C protrude radially from the tubular portion 20A in a sort of flange. The two side wings 20C extend from the tubular portion 20A in directions opposite one another. The previously mentioned hole 20B is arranged offset at a 90° angle to the respective side wing 20C, as is shown in FIG. 6.

Each side wing 20C has an opening 20D in a size that enables the operator's finger to be pushed through.

The tension wire is anchored on the slider 20. Thus, the slider 20 forms the proximal anchoring point of the tension wire (tension wires). The tension wire is anchored, e.g., on the inner circumference of the slider 20.

A pintle 30 in inserted, as a locking means, in the hole 20B of the tubular portion 20A of the slider 20. The pintle 30 is formed as a cylinder pin flattened on one side, the cross-section of which has the form of the letter D. On the non-flattened side, the pintle 30 has an outer diameter that is greater than the gap width of the slit 14A. In the pintle 30 cross-section, the dimension from the flattened side to the opposite outer circumference is less than the gap width of the slit 14A. In other words, the pintle 30 has a first radial dimension, which is greater than the gap width of the slit 14A and a second radial dimension that is less than the gap width of the slit 14A.

The pintle 30 penetrates the slit 14A. The pintle 30 has a recess 30A, into which a tool can be inserted in a form-fitting manner, on the side pointing outward, in order to turn the pintle 30.

When the slider 20 is pushed on and relative to the rod element 14, the pintle 30 has a relative position to the slider 20, in which the pintle 30, with its second radial dimension, which is less than the gap width of the slit 14A, is guided into the slit 14A.

Thus, by rotating the pintle 30, a selected longitudinal displacement position of the slider 20, relative to the rod element 14, can be arrested, in which the pintle 30 is rotated relative to the slider 20 such that its first radial dimension is effective at the sidewalls of the slit 14A.

When it is placed in the endoscope, the working channel element 1 can be mounted on the endoscope by means of a mounting means 50. To this end, the endoscope 100 itself has a customary Luer-Lock connection on its connecting element 104, which with the mounting means 50 of the working channel element 1 engages.

Figure 7:
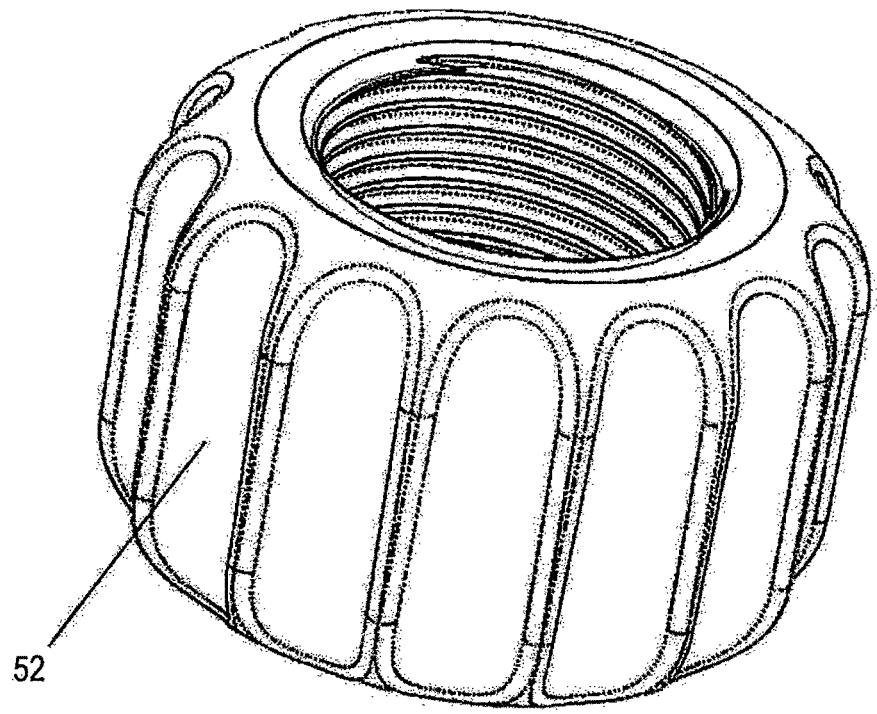
FIG. 7 shows a perspective view of elements of a mounting means of the working channel element according to the invention of the first exemplary embodiment.
Figure 7:
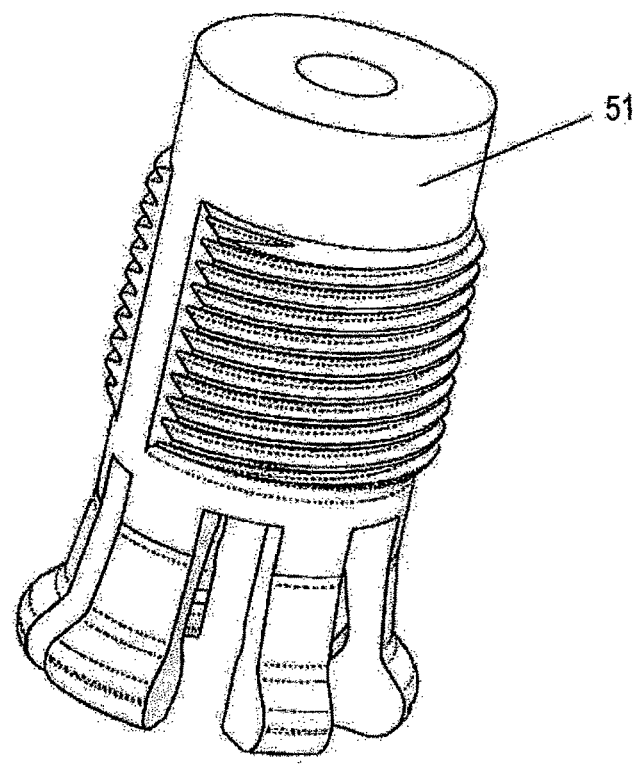

FIG. 7 shows the elements of the mounting means 50. Specifically, the mounting means 50 consists of a Luer-Lock counterpart 51 mated to the Luer-Lock connection of the endoscope 100 and a threaded cap 52 placed on the Luer-Lock counterpart 51.

The Luer-Lock counterpart 51 is located on the outer circumference of the working channel element 1, approximately in the area in which the tube 2 (main tube 12) and the transition element 13 meet. The Luer-Lock counterpart 51 sits firmly on the outer circumference of the working channel element 1. The Luer-Lock counterpart 51 is arrested on the Luer-Lock connection of the endoscope 100 by means of a threaded cap 52.

Because such a Luer-Lock system is a standardized connection system for tube systems in the medicinal sector, it does not have to be explained in further detail here.

Upon a tensile movement of the slider 20 in the proximal direction, the bending portion 11 is bent toward the outside on the lateral side, on which the tension wire is distally anchored.

The working channel element 1 is thus pushed into the endoscope 100 such that the radial side of the bending portion 11, on which the distal anchoring point of the tension wire is arranged, is located on the radial side opposite the ultrasound sensor 102.

Function of the Invention

In the present invention, thus a working channel element 1 separate from the endoscope 100 is inserted into the working channel 101 of the endoscope 100. Specifically, the working channel element 1 is inserted into the working channel 101, from the proximal side of the working channel 101, with the distal side of the working channel element 1 ahead.

Once the working channel element 1 has been completely inserted into the working channel 101 of the endoscope 100, the working channel element 1 is mounted on the endoscope 100 by means of the mounting means 50 (Luer-Lock). In said mounted position, the radial side of the bending portion 11, in which the tension wire is anchored, points toward the radial side opposite the ultrasound sensor 102.

Thus, the endoscope 100 equipped with the working channel element 1 is ready for use. The endoscope 100 equipped with the working channel element 1 is introduced into the patient at the desired usage point (e.g. the bile duct).

Then, by pushing the slider 20 into the proximal direction, the operator can bend the bending portion 11 on the distal end of the working channel element 1 to a desired position. Once the desired bent position of the bending portion 11 is achieved (e.g. opposite the bile duct), the position of the slider 20 is arrested by means of the locking means 30.

An instrument (micro-tool) can then be pushed through the working channel element 1 and the necessary action can be executed with the instrument.

After the action is complete, the instrument is withdrawn. The slider 20 is then detached. By sliding the slider 20 in the distal direction, the tension wire is relaxed whereby the bending portion 11 is straightened. The endoscope can then be removed from the patient.

The mounting means 50 is then detached and the working channel element 1 is removed from the endoscope 100 and disposed of.

Thus, the working channel element 1 is only arranged temporarily in the endoscope 100. After the working channel element has been used once, it is pulled out of the endoscope 100 and is disposed of. Whereas the endoscope 100 is then reprocessed.

Effects of the Invention

In endoscopes, the working channel element 1 according to the invention can take over both the function of a conventional Albarran lever, which adjusts the angular position of instruments, as well as horizontal precise adjustment of the desired target position of the instrument. In this case, the controllable end piece is connected to a working channel, which itself is not permanently connected to the endoscope and can be removed from the endoscope.

The great advantage with this system is a simplified cleaning of the endoscope and a prevention of cross-contamination, because a different working channel is used with each patient and the complex geometry of a conventional Albarran lever is completely dispensed with for cleaning.

Exemplary Embodiment 2

In the present second exemplary embodiment, which is not shown in the drawings, the endoscope is a flexible endoscope with an Albarran lever. As in the first exemplary embodiment, a working channel element 1 according to the invention can be inserted into the endoscope. The working channel element 1 corresponds to the working channel element 1 of the first exemplary embodiment.

For the configuration described in the first exemplary embodiment, the endoscope additionally has a (not shown) control mechanism (e.g. a joystick) for actuating an Albarran lever (not shown) arranged on the distal end of the insertion portion B.

The working channel element 1 according to the invention of the second exemplary embodiment protrudes, after it has been inserted into the endoscope and mounted on the endoscope via mounting means, on the distal side from the distal end of the endoscope head. Specifically, the bending portion 11 of the working channel element 1 protrudes from the distal end of the endoscope head. The remaining configuration corresponds to the configuration of the first exemplary embodiment.

In the present second exemplary embodiment, the bending of the inserted instruments on the distal side is not only enabled merely by means of the bending portion 11 of the working channel element 1. The Albarran lever can take on the main bending of the distal end piece of the working channel element 1. In addition to this main bending, the operator can carry out a precise adjustment by means of a separate bending of the bending portion 11 of the working channel element 1.

To this end, it is sufficient for at least one part of the bending portion 11 to be arranged distally from the Albarran lever of the endoscope when the working channel element 1 is installed in the endoscope.

The controllability of the inserted instruments can be greatly thereby improved.

Exemplary Embodiment 3

In the first exemplary embodiment, the endoscope 1 is a flexible endoscope and the working channel element 1 has the bending portion 11, which can be bent through the control unit 20.

In the present third exemplary embodiment, which is not shown in the drawings, the endoscope is likewise a flexible endoscope. The endoscope has a working channel element 1 without a bending portion 11 and without a control unit 20.

Thus, a working channel element 1, which itself is not controlled, is inserted into the endoscope.

This configuration also results in the advantageous effect that, after use, the working channel element 1 according to the invention can be removed from the endoscope and disposed of. The endoscope is transferred to the cleaning process.

Thus, even in the third exemplary embodiment, microbes from a previous use can be prevented from remaining on the endoscope to be cleaned in the working channel area.

Exemplary Embodiment 4

In the first exemplary embodiment, the working channel element 1 is again removed from the endoscope 100 in the proximal direction after use. However, the invention is not limited thereto.

In the present fourth exemplary embodiment, the working channel element 1 is severed (e.g. cut through) in the area of the proximal end of the main tube 12 or in the area of the transition element 13. Only the control unit of the working channel element 1 is removed in the proximal direction. The contaminated part of the working channel element 1, that is the bending portion 11 and a distal part of the main tube 12, is removed from the endoscope 100 in the distal direction.

This ensures even better protection against cross-contamination, because the interior of the working channel 101 of the endoscope 100 does not come into contact with microbes.

In a sub-variation of the fourth exemplary embodiment, a predetermined breaking point is provided in the area of the proximal end of the main tube 12 or in the area of the transition element 13. The working channel element 1 can be bent and broken at the predetermined breaking point. This simplifies the separation of the working channel element 1 between the working channel element 1 control unit to be removed in the proximal direction and the contaminated part of the working channel element 1 to be removed from the endoscope 100 in the distal direction.

In addition, the control unit of the working channel element 1 can be reused with this sub-variation.

Exemplary Embodiment 5

Figure 9:
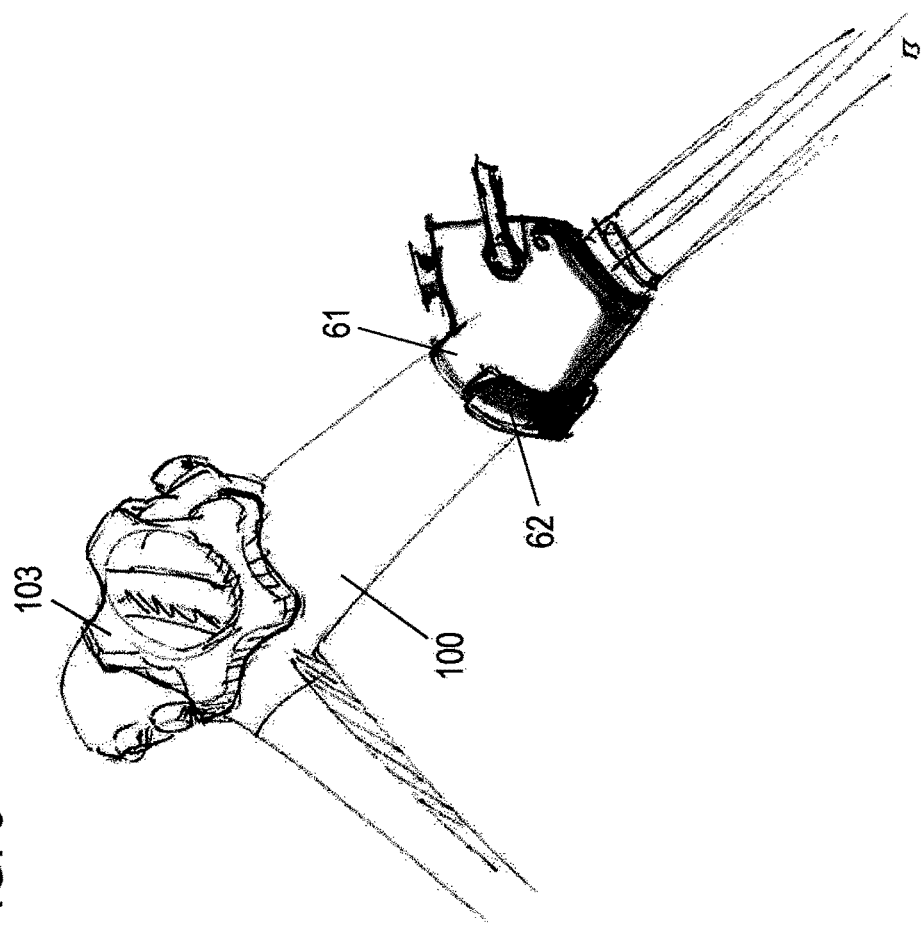
FIG. 9 shows a perspective view of the first application example of the working channel element according to the invention of the fifth exemplary embodiment in the state in which it is installed on the endoscope.
Figure 8:
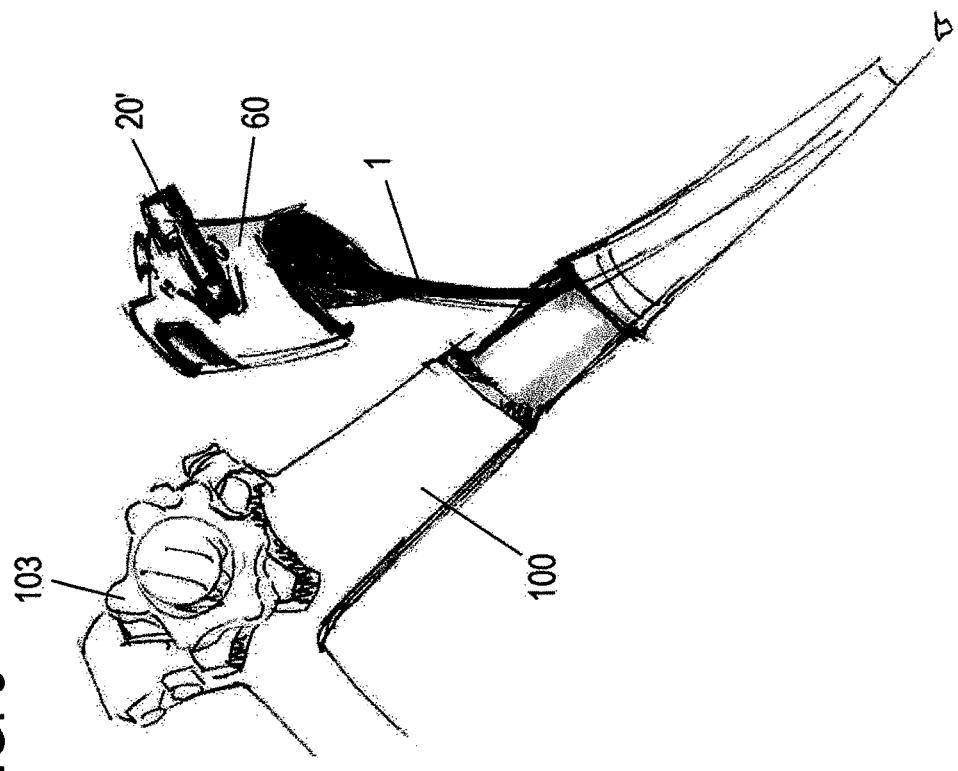
FIG. 8 shows a perspective view of a working channel element according to the invention of a fifth exemplary embodiment.

A further exemplary embodiment is shown in FIGS. 8 and 9.

FIG. 8 shows a working channel element 1 of the fifth exemplary embodiment in a situation in which it is being attached to an endoscope 100. FIG. 9 shows the working channel element 1 of the fifth exemplary embodiment in a situation in which the mounting of the working channel element 1 to the endoscope 100 is complete.

The working channel element 1 of the fifth exemplary embodiment has a control unit 20' facing the opposite direction of the control unit 20 of the first exemplary embodiment. Instead of the slider 20, the control unit is formed as a lever 20' in this case. The lever 20' has a base area, to which the control wires are mounted such that they are tensioned when a pivot movement of the lever 20' is executed.

The proximal area of the working channel element 1 of the fifth exemplary embodiment is integrated into a housing part 60, from the outer surface of which the lever 20' extends.

The housing part 60 has a housing piece 61, which has an area that is adapted to the outer contour of a gripping portion of the endoscope 100 such that it can be clipped onto the gripping portion of the endoscope 100. The housing piece 61 has a closure element 62, by means of which the housing piece 61 is secured to the endoscope 100, at a suitable location; see FIG. 9. The closure element is not limited to a closure element 62 as in FIG. 9. Any types and forms of a closure element can be used.

The proximal area of the working channel element 1 is integrated into the interior of the housing piece 61. For example, the lever 20' may have a shaft (not shown). The lever 20' may pivot about said shaft. Said shaft is pierced by a portion of the working channel element 1 which corresponds to the rod element 14 of the first exemplary embodiment. The tension wires are wound about the shaft on the interior of said portion of the working channel element 1. Thus, the tension wires can be tensioned upon execution of a pivot movement of the lever 20'.

Any other tensioning options of the tension wires can also be used here by means of the lever 20'.

In the fifth exemplary embodiment, the working channel element 1 can be easily and quickly attached to the gripping area of the endoscope 100 after insertion into the working channel of the endoscope 100. Both the control unit 103 of the endoscope 100 and the lever 20' are easily accessible and actuatable for the operator.

Such an endoscope as is used in the fifth exemplary embodiment can be designed such that its distal end can only be actuated by means of the clipped-on working channel element 1. Thus, such an endoscope cannot be used without the clipped-on working channel element 1.

Exemplary Embodiment 6

Figure 11:
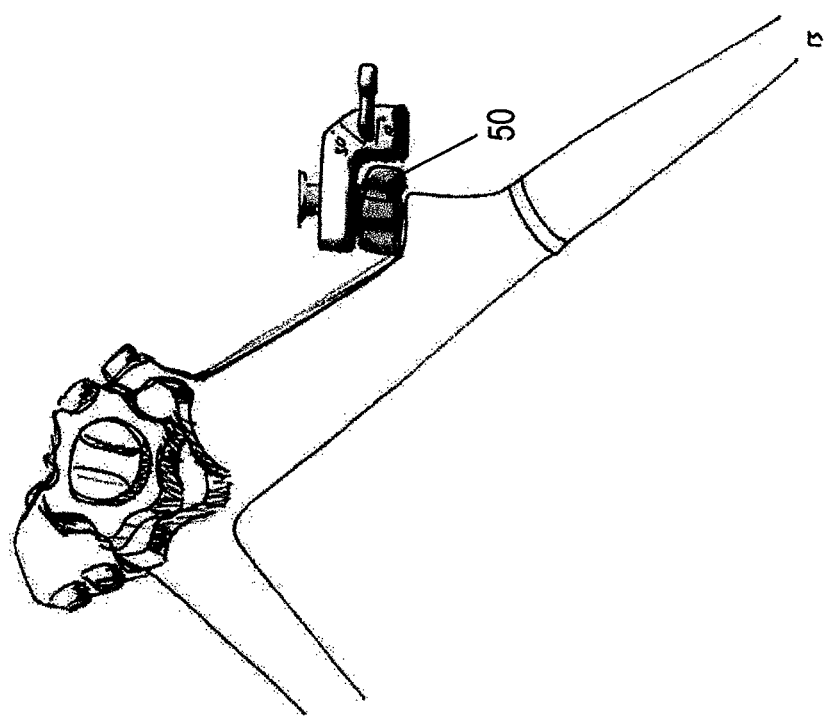
FIG. 11 shows a perspective view of the second application example of the working channel element according to the invention of the sixth exemplary embodiment in the state in which it is installed on the endoscope.
Figure 10:
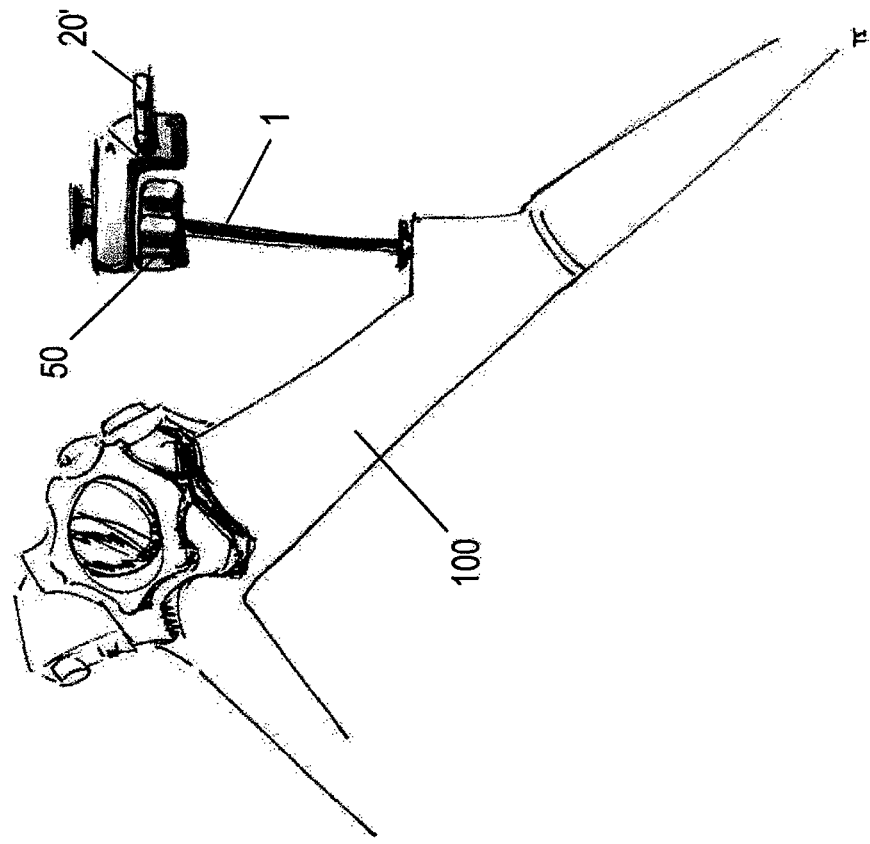
FIG. 10 shows a perspective view of a working channel element according to the invention of a sixth exemplary embodiment.

A further exemplary embodiment is shown in FIGS. 10 and 11.

FIG. 10 shows a working channel element 1 of the sixth exemplary embodiment in a situation in which it is being attached to an endoscope 100. FIG. 11 shows the working channel element 1 of the sixth exemplary embodiment in a situation in which the mounting of the working channel element 1 to the endoscope 100 is complete.

The working channel element 1 of the sixth exemplary embodiment has a control unit facing opposite the control unit 20 of the first exemplary embodiment, which, similarly to the fifth exemplary embodiment, is configured as a lever 20'.

The proximal area of the working channel element 1 of the sixth exemplary embodiment is mounted and secured to the endoscope 100 by means of Luer-Lock, as in the first exemplary embodiment.

In the sixth exemplary embodiment as well, the working channel element 1 can be easily and quickly attached to the gripping area of the endoscope 100 after insertion into the working channel of the endoscope 100. Both the control unit 103 of the endoscope 100 and the lever 20' are easily accessible and actuatable for the operator.

Such an endoscope as is used in the sixth exemplary embodiment can be designed such that its distal end can also be actuated without the working channel element 1. Thus, such an endoscope can also be used without the mounted-on working channel element 1.

The previously explained exemplary embodiments may be suitably combined.

FURTHER EXEMPLARY EMBODIMENTS AND ALTERNATIVES

The present invention may be preferably used with a duodenoscope as described but is not limited thereto. The present invention can be used with a gastroscope, a colonoscope, or a similar endoscope as well. The principle of the invention can be applied as well, however, to any other type of endoscope.

In the exemplary embodiment, the endoscope is a flexible endoscope. The endoscope may also be configured as a rigid endoscope in which the working channel element 1 according to the invention can be used.

In the first exemplary embodiment, the ultrasound sensor 102 is arranged on the distal end of the endoscope head 108. The ultrasound sensor 102 can also be omitted.

In an alternative, in the first exemplary embodiment, two tension wires can be provided in the working channel element 1, which are anchored relatively close to one another on one side of the circumference, on the distal end of the working channel element 1. The tension wires may be arranged such that they are not spaced 180° apart from one another, i.e. the tension wires are arranged close to one another along the circumference of the tubular element 2, on one side of the circumference. On the distal side of the tubular element 2, that is in the bending portion 11, the tension wires are guided to the distal annular element through the proximal annular element and the tubular piece of the bending portion 11 and anchored on the distal annular element. In this case as well, the distal annular element forms the distal anchoring point of the tension wires.

In the arrangement of the tension wires relative to the working channel element 1, two tension wires may be arranged close to one another, in a further alternative, along the circumference (short distance) on the distal end, and be arranged 180° apart from one another (equal distance) on the proximal side on the slider 20. The distance between the individual tension wires with respect to one another as measured in the circumferential direction is thus modified along the entire tubular element 2. As in the first exemplary embodiment, upon a tensile movement of the slider 20 in the proximal direction, the bending portion 11 is bent toward the outside on the lateral side, on which the two tension wires are distally anchored.

Alternatively, even three or four or more tension wires can be provided in the working channel element 1 according to the invention. If three or more tension wires are used, they may also be anchored relatively close to one another on one side of the circumference on the distal end of the working channel element 1.

In order to improve the control accuracy, the three or more tension wires may alternatively be anchored on the circumference on the distal end of the working channel element 1 such that two (of three), three (of four), etc. of the tension wires are relatively close to one another on one side of the circumference, and one tension wire is anchored on the opposite circumferential side. In this alternative, the slider 20 is provided so as to pivot about the rod element 14 (about its own axis). The respective tension wires can each be tensioned differently by pulling and pivoting the slider 20 relative to the rod element 14. For example, for an illustrative specific example of this alternative, the tension wires can be anchored at the 12 o'clock, 1 o'clock, 6 o'clock, and 11 o'clock positions on the circumference, on the distal end of the working channel element 1. The locking means 30 is then not formed as a pin going through the slit 14A but rather, e.g., as a clamping mechanism on the slider 20 functioning on the circumference of the rod element 14.

Moreover, the control unit 20 is not limited to the slider or the lever. For example, a handwheel can be used as the control unit 20. Any preferred mechanism that can tension the tension wires individually or as a group can be used.

The control unit 20 does not necessarily have to consist of only one mechanism. Two or more mechanisms, which are assigned to one or a group of tension wires, can also be used. The control accuracy can thereby be even further improved. For example, the slider 20 of the first exemplary embodiment can be divided into two slider elements in the axial direction in the axis area, each of which forms a side wing 20C and overlaps with one another in the axial area. Instead of the tubular portion 20A, each side wing 20C has a partial tubular portion 20A, one of which overlaps the other. At least one tension wire is anchored in both side wings 20C, and the side wings 20C can be pushed relative to one another along the rod element 14. Instead of the hole 20B, a corresponding slit extending axially is provided in both side wings 20C on the partial tubular portion 20A. In this alternative, the tension wires can be controlled separately.

The invention is not limited to a specific type of control unit. Any type of control unit for controlling the tension wires can be used.

In the present invention, a tension wire is described for controlling the bending of the distal end of the working channel element 1. The term "tension wire" does not only refer to a wire in the general sense. A drawing cable or a Bowden design can also be used as the "tension wire." Furthermore, the material of the "tension wire" is not subject to any limitations. The "tension wire" must only be capable of transferring a force of any control mechanism to the distal end of the working channel element 1 in order to control the direction and/or the angle and/or the extent of the bending of the distal end of the working channel element 1.

The working channel element according to the invention may also be formed without a bending portion 11. In this alternative, a control unit for controlling the bending is also not necessary. Such a working channel element also offers the advantage that the actual working channel of the endoscope, into which the working channel element is being inserted, is not contaminated during use. Prevention of cross-contamination is also possible in this alternative, because a different working channel is used for each patient.

LIST OF REFERENCE SYMBOLS

1 Working channel element
2 Tube
11 Bending portion
12 Main tube
13 Transition element
14 Rod element
14A Slit
15 Nose
16 Plate element
17 Instrument access
20 Control unit, slider
20' Control unit, lever
20A Tubular portion
20B Hole
20C Side wing
20D Opening
30 Locking means, pintle
50 Mounting means
51 Luer-Lock counterpart
52 Threaded cap
60 Housing part
61 Housing piece
62 Closure element
100 Endoscope
101 Working channel of the endoscope
102 Ultrasound sensor of the endoscope
103 Control unit of the endoscope, adjusting knob
104 Connection for working channel element
105 Gripping portion
106 Cable
107 Endoscope bending portion
108 Endoscope head
A Control part
B Insertion portion

The invention claimed is:

1. A working channel instrument for an endoscope, the working channel instrument comprising:
   a working channel element having a tubular shape which has an inner circumference and an outer circumference and through which an instrument can be pushed;
   a bending portion located on a distal side of the working channel element;
   an actuator that controls the bending of the bending portion, the actuator comprising a hollow cylinder rod element having has a lateral slit extending in a longitudinal direction of the hollow cylinder rod element, wherein the actuator is located on a proximal side thereof;
   a slider arranged on the hollow cylinder rod element and configured to slide along on the hollow cylinder rod element in the longitudinal direction thereof;
   a tension wire anchored on the slider such that the bending portion is bendable by the tension wire; and
   a lock located on the slider, wherein in the lock is:
      guidable in the lateral slit of the hollow cylinder rod element, and
      lockable in a selected longitudinal displacement position of the slider relative to the hollow cylinder rod element, and
   wherein the working channel element is adapted to be temporarily inserted into a working channel of an endoscope by its distal side.

2. The working channel instrument according to claim 1, wherein
   the actuator is configured such that it tensions at least one said tension wire guided in the working channel element between the inner circumference and the outer circumference and anchored at the bending portion, so as to control the bending of the bending portion.

3. The working channel instrument according to claim 2, wherein
   the proximal end of the control wire is anchored to the slider.

4. The working channel instrument according to claim 1, wherein
   the lock is positioned on the proximal side of the working channel element and is configured to fix a bent position of the bending portion.

5. The working channel instrument according to claim 1, wherein
   the working channel element comprises, on the proximal side, a mount by which the working channel element can be mounted to an endoscope.

6. An endoscope comprising the working channel instrument according to claim 1.

7. A method for using a working channel in an endoscope, the method comprising:
   temporarily inserting a separate working channel element is, with its distal side first, into a working channel of an endoscope, wherein:
      the working channel element has a tubular shape which has an inner circumference and an outer circumference and through which an instrument can be pushed, and
      the working channel element has a bending portion located on a distal side thereof;
   controlling, via an actuator, the bending of the bending portion, the actuator including a hollow cylinder rod element having has a lateral slit extending in a longitudinal direction of the hollow cylinder rod element, wherein the actuator is located on a proximal side thereof;
   sliding a slider arranged on the hollow cylinder rod element along on the hollow cylinder rod element in the longitudinal direction thereof;
   bending the bending portion via a tension wire anchored on the slider;
   guiding a lock located on the slider in the lateral slit of the hollow cylinder rod element; and
   locking the lock in a selected longitudinal displacement position of the slider relative to the hollow cylinder rod element.

8. The method according to claim 7, further comprising:
   bending a distal end of the working channel element to the desired position.

9. The method according to claim 7, further comprising:
   after the working channel element has been used once, pulling the working channel element out of the endoscope and disposing of the working channel element.

10. The method according to claim 9, wherein
    the pulling of the working channel element out of the endoscope comprises pulling the working channel element out of the endoscope on the distal side of the endoscope.

* * * * *